United States Patent

Benthien et al.

(10) Patent No.: US 6,656,425 B1
(45) Date of Patent: Dec. 2, 2003

(54) SILANE-BASED COATING WITH A DEODORIZING EFFECT FOR DOMESTIC APPLIANCES

(75) Inventors: Thomas Benthien, Landsberg am Lech (DE); Stefan Faber, Wadern (DE); Gerhard Jonschker, Spiesen-Elversberg (DE); Stefan Sepeur, Wadgassen-Schaffhausen (DE); Helmut Schmidt, Saarbruecken-Guedingen (DE); Philipp Stoessel, Saarbruecken (DE); Frank Joerdens, Traunreut (DE); Gerhard Schmidmayer, Bad Endorf (DE)

(73) Assignees: Institut für Neue Materialien gem. GmbH, Saarbrücken (DE); BSH Bosch und Siemens Hausgeräte GmbH, München (DE)

( * ) Notice: Subject to any disclaimer, the term of this patent is extended or adjusted under 35 U.S.C. 154(b) by 0 days.

(21) Appl. No.: 09/958,199

(22) PCT Filed: Apr. 5, 2000

(86) PCT No.: PCT/EP00/03021

§ 371 (c)(1),
(2), (4) Date: Jun. 11, 2002

(87) PCT Pub. No.: WO00/59555

PCT Pub. Date: Oct. 12, 2000

(30) Foreign Application Priority Data

Apr. 5, 1999 (DE) .......................... 199 15 378

(51) Int. Cl.[7] .................................................. A61L 2/00
(52) U.S. Cl. ................. 422/5; 422/4; 422/120; 422/122
(58) Field of Search ................. 422/4, 5, 120, 422/122

(56) References Cited

U.S. PATENT DOCUMENTS

| | | | | |
|---|---|---|---|---|
| 4,510,219 A | * | 4/1985 | Rowlette | 429/212 |
| 5,326,633 A | * | 7/1994 | Clough et al. | 442/110 |
| 6,124,491 A | * | 9/2000 | Wolter et al. | 556/438 |

FOREIGN PATENT DOCUMENTS

EP  459003 A1 * 12/1991

* cited by examiner

Primary Examiner—Krisanne Thornton
(74) Attorney, Agent, or Firm—Heller Ehrman White & McAuliffe LLP

(57) ABSTRACT

Domestic appliances are provided with a catalytic deodorizing coating, prepared by applying a coating material containing a polycondensate of at least one hydrolysable organosilane, optionally one or more compounds of glass-forming elements, and particles of one or more catalytically active transition metal oxides, and then heat-treating the applied coating material.

9 Claims, No Drawings

SILANE-BASED COATING WITH A DEODORIZING EFFECT FOR DOMESTIC APPLIANCES

The invention relates to domestic appliances comprising a catalytic composition for the purpose of deodorizing and oxidizing organic components or carbon.

An object of the present invention is to provide catalytic compositions for domestic appliances which are capable of reducing or eliminating environmental odour pollution (deodorizing) and which are able to oxidize organic components or carbon.

This objective is surprisingly achieved by means of domestic appliances having a catalytic composition which comprises a coating of a coating material on a support and is obtainable by applying the coating material, comprising (1) a polycondensate of (A) one or more silanes of the general formula (I)

$$R_a—Si—X_{(4-a)} \quad (I)$$

in which the radicals R are identical or different and are non-hydrolysable groups, the radicals X are identical or different and are hydrolysable groups or hydroxyl groups and a has the value 0, 1, 2 or 3, with a being greater than 0 for at least 50 mol % of the silanes, or an oligomer derived therefrom, (B) if desired, one or more compounds of glass-forming elements, and (2) particles of one or more transition metal oxides, the weight ratio of transition metal oxide particles to polycondensate being from 10:1 to 1:10, to the support and subjecting the applied coating material to thermal treatment, said catalytic composition representing a component of said domestic appliance or of a device connected with said domestic appliance.

In the hydrolysable silanes (A), the hydrolysable groups X are, for example, hydrogen or halogen (F, Cl, Br or I), alkoxy (preferably $C_{1-6}$ alkoxy, such as methoxy, ethoxy, n-propoxy, i-propoxy and butoxy), aryloxy (preferably $C_{6-10}$ aryloxy, such as phenoxy), acyloxy (preferably $C_{1-6}$ acyloxy, such as acetoxy or propionyloxy), alkylcarbonyl (preferably $C_{2-7}$ alkylcarbonyl, such as acetyl), amino, monoalkylamino or dialkylamino having preferably from 1 to 12, in particular from 1 to 6, carbon atoms.

The non-hydrolysable radicals R may be non-hydrolysable radicals $R^1$ or may be radicals $R^2$ which carry a functional group, $R^1$ being preferred.

The non-hydrolysable radical $R^1$ is, for example, alkyl (preferably $C_{1-8}$ alkyl, such as methyl, ethyl, n-propyl, isopropyl, n-butyl, s-butyl and t-butyl, pentyl, hexyl, octyl or cyclohexyl), alkenyl (preferably $C_{2-6}$ alkenyl, such as vinyl, 1-propenyl, 2-propenyl and butenyl), alkynyl (preferably $C_{2-6}$ alkynyl, such as acetylenyl and propargyl) and aryl (preferably $C_{6-10}$ aryl, such as phenyl and naphthyl). The stated radicals $R^1$ and X may if desired have one or more customary substituents, such as halogen or alkoxy, for example.

Specific examples of the functional groups of the radical $R^2$ are the epoxy, hydroxyl, ether, amino, monoalkylamino, dialkylamino, amide, carboxyl, vinyl, acryloyloxy, methacryloyloxy, cyano, halogen, aldehyde, alkylcarbonyl, and phosphoric acid group. These functional groups are attached to the silicon atom via alkylene, alkenylene or arylene bridging groups, which may be interrupted by oxygen or —NH— groups. The stated bridging groups are derived, for example, from the abovementioned alkyl, alkenyl or aryl radicals. The radicals $R^2$ contain preferably from 1 to 18, in particular from 1 to 8, carbon atoms.

In one preferred embodiment, the silanes (A) comprise a mixture of (A1) at least one hydrolysable silane of the general formula (II)

$$SiX_4 \quad (II)$$

in which the radicals X are identical or different and are hydrolysable groups or hydroxyl groups, or an oligomer derived therefrom, and (A2) at least one organosilane of the general formula (III), $$R^1_{a1}R^2_{a2}SiX_{(4-a1-a2)} \quad (III)$$

in which $R^1$ is identical or different at each occurrence and is a non-hydrolysable group, $R^2$ is identical or different at each occurrence and is a radical which carries a functional group, X has the above definition and a1 and a2 have the value 0, 1, 2 or 3, the sum (a1+a2) having the value 1, 2 or 3, or an oligomer derived therefrom in a molar ratio (A1):(A2) of 5-50:50-95.

In the general formula (III), a1 preferably has the value 1 or 2, a2 preferably has the value 0, 1 or 2 and the sum (a1+a2) preferably has the value 1 or 2.

Particularly preferred hydrolysable silanes (A) and (A1) are tetraalkoxysilanes such as tetraethoxysilane (TEOS). Particularly preferred hydrolysable silanes (A) and (A2) are alkyltrialkoxysilanes, preferably containing $C_1$–$C_8$ alkyl, especially methyltriethoxysilane, aryltrialkoxysilanes, especially phenyltriethoxysilane, dialkyldialkoxysilanes, preferably containing $C_1$–$C_8$ alkyl, especially dimethyldiethoxysilane, and diaryldialkoxysilanes, especially diphenyldiethoxysilane. Silanes containing functional groups (A) and (A2) are, for example, epoxy silanes such as 3-glycidyloxypropyltrimethoxysilane (GPTS) and amino silanes such as 3-aminopropyltriethoxysilane and 3-(aminoethylamino)propyltriethoxysilane (DIAMO).

In the silane component (A) according to formula (I), a is greater than 0 for at least 50 mol % of the silanes, i.e. at least 50 mol % of the silanes contain at least one non-hydrolysable group R. The silane component (A) preferably comprises from 50 to 95 mol % of silanes having at least one non-hydrolysable group R. With regard to the formulae (II) and (III), the preferred molar ratio of the hydrolysable silane (A1) to the organosilane (A2) in the polycondensate is 5 to 50:50 to 95, preferably from 1:1 to 1:6 and with particular preference from 1:3 to 1:5. A particularly favourable molar ratio is 1:4.

The optional component (B) constitutes glass-forming elements which are preferably dispersible or soluble in the reaction medium. It is possible to use, for example, compounds (halides, alkoxides, carboxylates, chelates, etc.) of lithium, sodium, potassium, rubidium, caesium, beryllium, magnesium, calcium, strontium, barium, boron, aluminium, titanium, zirconium, tin, zinc or vanadium.

To prepare the polycondensate (1), the starting components (A) and, where appropriate, (B) are hydrolysed and condensed. The hydrolysis and condensation are conducted either in the absence of a solvent or, preferably, in an aqueous or aqueous/organic reaction medium, where appropriate in the presence of an acidic or basic condensation catalyst such as HCl, $HNO_3$ or $NH_3$. The hydrolysis and condensation preferably take place in the presence of an aqueous acid. The aqueous acids are used preferably in a concentration range of from 0.1 N to 10.0 N. Acids used with preference are hydrochloric, nitric, phosphoric and acetic acid.

Additionally, during the preparation of the polycondensate, the inorganic particles set out below may be added. During the preparation, preferably, nanoscale inorganic particles, especially in the form of a sol, are added. By way of example, silica sols may act as hydrolytically active compounds in the sol. Suitable for this purpose are commercially customary silica sols, such as the Levasils®, silica sols from Bayer AG, for example.

When a liquid reaction medium is used, the starting components are soluble in the reaction medium. Particularly suitable organic solvents are water-miscible solvents, such as monohydric or polyhydric aliphatic alcohols, for example, but also aliphatic or aromatic hydrocarbons, such as those having from 5 to 20 carbon atoms, ethers, esters, ketones, amides and alkylamides.

The hydrolysis and polycondensation preferably take place under the conditions of the sol-gel process, the reaction mixture being used in the viscous sol state to coat the substrate.

Where appropriate, the hydrolysis and polycondensation are carried out in the presence of a complexing agent, examples of such agents being nitrates, β-dicarbonyl compounds (e.g. acetylacetonates or acetoacetates), carboxylic acids (e.g. methacrylic acid) or carboxylates (e.g. acetate, citrate or glycolate), betaines, diols, diamines (e.g. DIAMO) or crown ethers.

The ratio of the hydrolytically active components to the hydrolysable silanes (and, where appropriate, to the glass-forming elements) may be characterized by the value $R_{OR}$. The $R_{OR}$ value represents the molar ratio of water from the hydrolytically active components (water, aqueous acid, silica sol, etc.) to the abovementioned hydrolysable groups X from the silane components (and, where appropriate, the corresponding hydrolysable groups of the glass-forming elements). The sol obtained possesses, for example, an $R_{OR}$ value of from 0.1 to 10 and preferably from 0.2 to 2.

The polycondensate obtained is mixed, preferably in the form of a sol, with particles of one or more transition metal oxides, the ratio of transition metal oxide particles to polycondensate being from 10:1 to 1:10, preferably from 10:1 to 1:1 and with particular preference from 10:1 to 2:1. In the case of this ratio, account is taken for the polycondensate, with the exception of any other organic solvent, of the components added for the purpose of preparing the polycondensate (in particular the inorganic particles for preparing the condensate).

The average particle diameter of the transition metal oxides used is situated, for example, in a range from 10 nm to 20 μm. In the case of coated substrates which are to be used for improving odour, it is preferred to use transition metal oxide particles having an average particle diameter of from 1 to 20 μm.

The particles consist substantially, or preferably completely, of transition metal oxide. The transition metal oxide particles may be composed of one transition metal oxide or of transition metal oxide mixtures. In the case of the transition metal oxide mixtures, which are used with preference, it is preferred to combine different transition metal oxide powders with one another so as to give particles comprising different transition metal oxides. It is of course also possible to use particles which contain different transition metal oxides.

In the case of use for oxidation purposes in particular, however, it is possible, besides the particles consisting essentially of transition metal oxides, to make additional use, in whole or in part, of particles which have the transition metal oxides indicated below at the surface but which otherwise are composed of a different material. In that case the transition metal oxide particles are composed of particles of a material chosen preferably from one of the materials specified below for the inorganic particles, said material being surface-coated with one or more transition metal oxides. Preferably, these particles are coated fully on the surface with the transition metal oxides. For the weight ratio of transition metal oxide particles to polycondensate, these particles are taken into account as a whole as transition metal oxide particles. The particles in question are in particular the particles in the micrometre range, indicated below, which have been provided on the surface, and/or impregnated, with transition metal oxides.

The transition metal oxides in question are, in particular, catalytically active transition metal oxides which have deodorizing and/or oxidizing properties. By transition metals are meant, as is customary, the elements of transition groups I to VIII of the Periodic Table and the lanthanide and actinide elements. With particular preference the transition metal oxide is selected from the oxides of the metals La, Ce, Ti, Zr, V, Cr, Mo, W, Mn, Fe, Co, Ni, Cu, Ag and Zn or from mixtures of these metal oxides. Preference is given to using transition metal oxide mixtures, with mixtures of the oxides of Mn and Ce with one or two further transition metals, such as mixtures of the oxides of Mn/Co/Ce, Mn/Cu/Ce, Mn/Ni/Ce, Mn/Fe/Ce or Mn/Co/Ni/Ce, being particularly preferred. A further-preferred transition metal oxide mixture is a mixture of the oxides of Cu/V/La. It is also possible to use mixed oxides of the aforementioned transition metals.

In the transition metal oxide mixtures, the following amounts of the corresponding metal oxides in the metal oxide mixture are preferred: Ce: 1–70% by weight, V: 5–70% by weight, Mn: 20–95% by weight, Fe: 20–95% by weight, Co: 1–50% by weight, Ni: 1–50% by weight, Cu: 1–95% by weight.

Specific examples of transition metal oxides are $MnO_2$ (pyrolusite), $\gamma\text{-}MnO_2$, $Co_3O_4$, $CO_2O_3$, $COO$ and $CeO_2$. It is of course also possible to use any other suitable transition metal oxide.

The BET surface area of the particles used is situated, for example, within a range from 1 to 100 $m^2/g$.

Besides the transition metal oxide particles, cocatalysts may also be used in the coating material, in amounts for example of from 1 to 5% by weight, based on the transition metal oxide particles. Suitable cocatalysts are, for instance, K, Mg, Ca, Ba and Sr salts and also Al oxide and Sn oxide. Examples of suitable salts are the corresponding halides, hydroxides, nitrates, carbonates, or phosphates. They may be added, for example, by mixing the cocatalyst with the transition metal oxide particles or with the mixtures of the transition metal oxide particles prior to addition to the polycondensate, or by separate addition of the cocatalyst to the coating material. In the former case, it is preferred to use powders, and in the latter case it is preferred to use readily soluble salts of the cocatalyst.

The coating material may also include inorganic particles, which may be added during the preparation of the polycondensate or of the coating material or thereafter. These particles may be nanoscale inorganic particles or particles in the micrometre range. It is also possible to add particles of both orders of magnitude, in which case the particles in the micrometre range are employed in particular when the catalytic composition is used for oxidizing organic components or carbon.

The inorganic particles may be composed of any desired materials, with oxides being preferred. Preferred oxides are oxides of Si and Al (especially boehmite). The particles may be added, for example, in the form of powders or, especially the nanoscale particles, in the form of sols.

The nanoscale inorganic particles preferably possess an average particle size of up to 300 nm, in particular up to 100 nm and with particular preference up to 50 nm. The particles may be added in colloidal form. In this case they can comprise sols or dispersible powders. Specific examples of nanoscale inorganic particles are $SiO_2$, $Al_2O_3$, $SnO_2$, iron oxides or carbon (carbon black and graphite), especially $SiO_2$. Very particular preference is given to using silica sols as nanoscale inorganic particles.

Especially if the catalytic compositions are to be used as oxidative compositions, inorganic particles in the micrometre range may also be added to the coating material. They serve to structure the coating and to produce cavities. These particles possess an average particle diameter of, for example, from 1 to 500 $\mu$m, preferably from 10 to 300 $\mu$m. They are preferably oxide- and/or hydroxyl-containing compounds of the elements from main groups III and IV, such as aluminium oxides or silicon oxides. They may have been activated. Examples that may be mentioned include kieselguhr, alumina 90, silica gel 40 or silica gel 60, produced by the company Merck.

Prior to their use, the abovementioned inorganic particles in the micrometre range may be impregnated with metal salts or mixtures of metal salts, such as chlorides, phosphates, formates, nitrates or acetates, and then treated at elevated temperatures in order to generate catalytically active metal oxides on the surface. Preference is given to using metal nitrates or metal acetates, since the anions form volatile products when treated within the temperature range used. Metals used are the transition metals specified for the transition metal oxide particles. In this case particles are obtained which are provided on the surface with transition metal oxides, which are used in accordance with the invention as transition metal oxide particles, and which are taken into account as a whole for the weight ratio of transition metal oxide particles to polycondensate.

The coating material may also comprise further additives. It is possible, for example, to use additives suitable for adjusting viscosity and/or, in particular, for generating cavities during the thermal treatment of the coating materials. For this purpose it is possible, for example, to use customary thickeners. Specific examples are cellulose derivatives, such as hydroxypropylcellulose, starch, modified starch, polyvinyl alcohol and glycols, e.g. polyethylene glycol. Preference is given to using cellulose derivatives, especially hydroxypropylcellulose. In addition it is also possible to use the additives customary in catalytic compositions, such as pigments (e.g. black pigments).

The viscosity of the sol mixed with the transition metal oxide particles may also be adjusted, if desired, by removing or adding a solvent, e.g. one of those mentioned above. In this form, the sol is usually also storable for long periods. Where appropriate, it may be activated by adding water or aqueous acid, in which case the coating material is preferably used within one month.

The coating material is applied to the support by customary coating methods. Applicable techniques are, for example, dipping, flow coating, spin coating, spraying or brushing.

Suitable supports are, for example, those of metals such as stainless steel, steel, copper, brass and aluminium; metal oxides, glasses such as float glass, borosilicate glass, lead crystal or silica glass; glass ceramics, and ceramics such as $Al_2O_3$, $ZrO_2$, $SiO_2$ mixed oxides, or else enamel, but also porous supports such as porous ceramics, for example. The shape of the supports is arbitrary. The supports in question may be planar or structured. Particularly suitable supports are those in the form of meshes, honeycombs or nets, such as wire meshes, examples being steel wire meshes, ceramic honeycombs or wire nets.

The supports may be pretreated prior to the application of the coating material. For example, they are subjected to cleaning, using commercially customary alkaline cleaners, for example. It is likewise possible, for example, by heat-treating steel supports and forming chromium oxide whiskers on the surface, to bring about substantially improved adhesion of the coating material to steel supports.

The resulting coating is subjected to initial drying, if desired, and then heat-treated. This can be done at temperatures of from 200° C. to 700° C., preferably from 300° C. to 400° C. The heat treatment may be carried out in air on in an inert gas such as nitrogen or argon. The heat treatment may also take place if desired by means of IR or laser radiation. The heat treatment may be accompanied, for example, by drying, curing or consolidation or compaction of the coating material.

The coating operation is preferably performed so as to give coat thicknesses of from 0.01 to 500 $\mu$m, preferably from 1 to 500 $\mu$m. Where the catalytic compositions are used for the purpose of deodorizing, coat thicknesses of from 30 to 100 $\mu$m, in particular from 25 to 75 $\mu$m, are preferred. Where the catalytic compositions are used as oxidatively active surfaces, coat thicknesses of from 1 to 10 $\mu$m are suitable when using transition metal oxides having an average particle size of less than 200 nm. The catalytic compositions which serve as oxidatively active surfaces, and which additionally comprise inorganic particles in the micrometre range, preferably have coat thicknesses of from 100 to 400 $\mu$m.

The catalytic compositions of the invention may have a porous or a non-porous coating. Preferably, the catalytic compositions have porous coatings. The pores may comprise microscopically visible cavities on the surface and/or relatively fine micropores. The cavities visible on the surface under the microscope have an approximately globular morphology (hemispheres) and their diameter is from about 1 to 5 $\mu$m. Their extent and form in the interior of the coat cannot be determined by microscopy. The determination of the BET surface areas of preferred embodiments indicates that relatively fine micropores are present therein alternatively or additionally.

The catalytic composition of the invention has a deodorizing effect; in other words, odour pollution caused by substances can be reduced or avoided completely. The deodorizing activity is found in particular at temperatures above 150° C., for example at temperatures from 150 to 500° C., preferably from 200 to 350° C. The odour-polluted air is guided past the catalytic composition at elevated temperatures. As it passes, substances present in the air are degraded.

The catalytic composition is also capable of oxidizing organic components or carbon, such as carbon black or graphite, which are present, for example, on the surface of the catalytic composition. The oxidizing activity is found in particular at the temperature ranges indicated above.

The catalytic compositions are preferably used for these purposes in such a way that they are located directly on any surface of the domestic appliance in question, in which case this surface acts as the substrate, or they represent a component of an additional device, connected where necessary via a connecting line, within or in the vicinity of the domestic appliance. The surface of the domestic appliance may, for instance, be part of the casing or an inner wall, preferably formed of metal. The additional device may, for instance, be an exhaust means of the domestic appliance. In addition to the catalytic composition, the additional device may e.g. comprise heating and venting means.

In this manner, the invention provides a simple way to combat malodors or surface staining which may occur in households and domestic appliances. Domestic appliances in accordance with the present invention are all articles and devices normally used in households. Suitable examples are stoves, stove-tops, kitchen vents and deep-fat fryers. Preferred field of application are electrical and gas stoves, kitchen vents and/or deep-fat fryers.

EXAMPLES

A. Preparation of the Silane Sols

Silane sol 1: MTKS sol, $R_{OR}$=0.4

A mixture of 1069.86 g (6.0 mol) of methyltriethoxysilane and 312.48 g (1.5 mol) of tetraethoxysilane is divided into two portions (portion 1 and portion 2) of equal weight.

To portion 1, 246.84 g of silica sol (Levasil 300/30, aqueous, basic, Bayer AG) are added with thorough stirring. After an emulsion has formed (about 30 s), 5.60 g of 36% strength by weight HCl are added. After brief stirring (30–50 s) the reaction mixture becomes clear with heating. Portion 2 is added quickly and all at once to this reaction mixture. After a short time, the reaction mixture becomes cloudy owing to a colourless precipitate (NaCl). This is followed by stirring with cooling in an ice bath for 15 minutes. The silane hydrolysate is left to stand at room temperature for 12 h and decanted from the sedimented solid, thus giving the ready-to-use MTKS sol.

Silane sol 2: MDKS sol, ROR=0.2

35.10 g of silica sol (Levasil 300/30, aqueous, basic, Bayer AG) and 1.10 g of 36% strength by weight HCl are added simultaneously to a mixture of 356.62 g (2.0 mol) of methyltriethoxysilane and 74.14 g (0.5 mol) of dimethyldiethoxysilane, with thorough stirring. After brief stirring (30–50 s) the reaction mixture becomes clear with heating. After a short time, the reaction mixture becomes cloudy owing to a colourless precipitate (NaCl). This is followed by stirring with cooling in an ice bath for 15 minutes. The silane hydrolysate is left to stand at room temperature for 12 h and decanted from the sedimented solid, thereby giving the ready-to-use MDKS sol.

Silane sol 3: MPTKS sol, ROR=0.4

3.29 g of silica sol (Levasil 300/30, aqueous, basic, Bayer AG) and 0.13 g of 36% strength by weight HCl are added simultaneously to a mixture of 11.59 g (0.065 mol.) of methyltriethoxysilane, 3.61 g (0.015 mol) of phenyltriethoxysilane and 4.17 g (0.020 mol) of tetraethoxysilane, with thorough stirring. After brief stirring (30–50 s) the reaction mixture becomes clear with heating. After a short time, the reaction mixture becomes cloudy owing to a colourless precipitate (NaCl). This is followed by stirring with cooling in an ice bath for 15 minutes. The silane hydrolysate is left to stand at room temperature for 12 h and decanted from the sedimented solid, thereby giving the ready-to-use MPTKS sol.

Silane sol 4: MPrTKS sol, ROR=0.4

7.00 g of silica sol (Levasil 300/30, aqueous, basic, Bayer AG) and 0.23 g of 32% strength by weight HCl are added simultaneously to a mixture of 15.00 g (0.084 mol) of methyltriethoxysilane, 14.95 g (0.091 mol) of n-propyltrimethoxysilane and 8.96 g (0.043 mol) of tetraethoxysilane, with thorough stirring. After brief stirring (30–50 s) the reaction mixture becomes clear with heating.

After a short time, the reaction mixture becomes cloudy owing to a colourless precipitate (NaCl). This is followed by stirring with cooling in an ice bath for 15 minutes. The silane hydrolysate is left to stand at room temperature for 12 h and decanted from the sedimented solid, thereby giving the ready-to-use MPrTKS sol.

Silane sol 5: MD sol, ROR=0.4

5.04 g of 0.1 N HCl are added to a mixture of 35.66 g (0.2 mol) of methyltriethoxysilane and 7.41 g (0.05 mol) of dimethyldiethoxysilane, with thorough stirring. After brief stirring (30–50 s) the reaction mixture becomes clear with heating. The silane hydrolysate is left to stand at room temperature for 12 h, thereby giving the ready-to-use MD sol.

B. Preparation of the Catalyst Mixtures

The catalyst mixtures used are mixtures of commercial transition metal oxide powders from Ferro or Aldrich:

$MnO_2$: Powder from Ferro, predominantly $MnO_2$ (pyrolusite), with a little γ-$MnO_2$ and a little $MnO_2$ $Co_yO_x$: Powder from Ferro, predominantly $Co_3O_4$, with a very little CoO Catalyst Mixture 1: Mn/Co/Ce Catalyst mixture 1 is prepared by intimately mixing 800.00 g of $MnO_2$, 100.00 g of $Co_yO_x$ and 100.00 g of $CeO_2$.

Catalyst Mixture 2: Mn/Co/Ce

Catalyst mixture 2 is prepared by intimately mixing 800.00 g of $MnO_2$, 150.00 g of $Co_yO_x$ and 50.00 g of $CeO_2$.

Catalyst Mixture 3: Mn/Cu/Ce

Catalyst mixture 3 is prepared by intimately mixing 650.00 g of $MnO_2$, 300.00 g of $Cu_2O$ and 50.00 g of $CeO_2$.

Catalyst Mixture 4: Mn/Co/Ni/Ce

Catalyst mixture 4 is prepared by intimately mixing 700.00 g of $MnO_2$, 100.00 g of $Co_yO_x$, 150.00 g of NiO and 50.00. g of $CeO_2$.

C. Preparation of the Coating Materials

Example 1

1000.00 g of catalyst mixture 1 are stirred at room temperature for 2 h with 300.00 g of silane sol 1 and 233.33 g of ethanol. Then 32.35 g of 10% strength by weight aqueous hydrochloric acid are added for activation (increasing the $R_{OR}$ value from 0.4 to 0.8), the mixture is stirred at room temperature for at least 2 h, and the ready-to-use coating suspension is obtained.

Example 2

1000.00 g of catalyst mixture 2 are stirred at room temperature for 2 h with 200.00 g of silane sol 1 and 350.00 g of ethanol. Then 23.49 g of 10% strength by weight aqueous hydrochloric acid are added for activation (increasing the $R_{OR}$ value from 0.4 to 0.8), the mixture is stirred at room temperature for at least 2 h, and the ready-to-use coating suspension is obtained.

Example 3

1000.00 g of catalyst mixture 3 are stirred at room temperature for 1 h with 400.00 g of silane sol 2 and 185.00 g of ethanol. Then 47.97 g of 10% strength by weight aqueous hydrochloric acid are added for activation (increasing the $R_{OR}$ value from 0.2 to 0.6), the mixture is stirred at room temperature for at least 4 h, and the ready-to-use coating suspension is obtained.

Example 4

1000.00 g of catalyst mixture 3 are stirred at room temperature for 1 h with 18.00 g of silane sol 3 and 25.00 g of ethanol. Then 1.52 g of 10% strength by weight aqueous hydrochloric acid are added for activation (increasing the $R_{OR}$ value from 0.4 to 0.7), the mixture is stirred at room temperature for at least 2 h, and the ready-to-use coating suspension is obtained.

Example 5

1000.00 g of catalyst mixture 4 are stirred at room temperature for 1 h with 40.00 g of silane sol 5 and 11.00 g of ethanol. Then 4.66 g of 10% strength by weight aqueous hydrochloric acid are added for activation (increasing the $R_{OR}$ value from 0.4 to 0.8), the mixture is stirred at room temperature for at least 2 h, and the ready-to-use coating suspension is obtained.

D. Coating and Heat Treatment (Especially for Deodorizing Purposes)

The support material used is steel wire mesh (diameter about 5 cm, height about 1 cm) or ceramic honeycombs. the steel meshes are first of all degreased using a commercial alkaline cleaner and then rinsed thoroughly with deionized water, before being dried at room temperature. The dry steel meshes are subsequently treated at 500° C. for 1 h.

Coating takes place by impregnating the steel wire meshes or the ceramic honeycombs in one of the coating materials (coating suspensions) described in section C. The excess coating suspension is removed by blowing with compressed air. After drying at room temperature (2 h), the coating is solidified by heat treatment. For this purpose the coated supports are heated from room temperature to 300–400° C. over the course of 1 h, held at 300–400° C. for 1 h, and then cooled to room temperature over 6 h.

Alternatively, the heat treatment may also be effected by direct placement of the dried, coated supports into an oven preheated to 300–400° C. and rapid cooling of the hot supports to room temperature over a few minutes.

The thicknesses of the thermally solidified coats are typically in the range 25–75 $\mu$m. The coat thicknesses may be set, for example, on the one hand by way of the viscosity of the coating suspension (which can be adjusted, for example, by adding an appropriate amount of ethanol), on the other by way of the pressure of the compressed air or the time of action of the compressed air during removal of the excess coating suspension.

E. Catalytic Composition 1 (Especially for Oxidizing)

E.1 Preparation of an Mn/Cu/Ce Catalyst on Alumina Particles 40.47 g (0.141 mol) of $Mn(NO_2)_2 \cdot 6 H_2O$, 11.63 g (0.050 mol) of $Cu(NO_3)_2 \cdot 3 H_2O$ and 15.20 g (0.035 mol) of $Ce(NO_3)_{3 \cdot 6} H_2O$ are dissolved in a mixture of 30.00 g of ethanol and 30.00 g of water at 50C. 100.00 g of alumina 90 (active, acidic (alternatively, neutral or basic can also be used), particle size 63–200 $\mu$m, from Merck) are added to this solution and the solvent mixture is evaporated off with stirring at 50–70° C. for 3 h. The alumina impregnated with the metal nitrates is subsequently treated at 500° C. for 1 h. Analogously, it is also possible to use the corresponding molar amounts of metal acetates or, instead of aluminium 90, the further Merck products silica gel 40, particle size 63–200 $\mu$m. silica gel 60, particle size 63–200 $\mu$m, or kieselguhr, particles size approximately 100 $\mu$m.

E.2 Coating Material 150.00 g of the above-described Mn/Cu/Ce catalyst (E.1) on the alumina particles are intimately mixed with 50.00 g of catalyst mixture 1. 100.00 g of a 5% strength by weight solution of hydroxypropylcellulose in ethanol are added with stirring to this mixture. 140.00 g of silane sol 2 are activated (increasing the $R_{OR}$ value from 0.2 to 0.8) by addition of 22.67 g (1.26 mol) of water, with stirring, and the mixture is stirred at room temperature for 30 minutes. The activated MDKS sol is added to the above-described mixture of Mn/Cu/Ce catalyst, catalyst mixture 1 and hydroxypropylcellulose in ethanol, at room temperature with stirring, and the mixture is then stirred at room temperature for 15 minutes to give the ready-to-use coating material.

E.3 Coating and Thermal Solidification

The support material used is steel substrates (metal panels 10×10 cm). The steel substrates are first of all degreased using a commercial alkaline cleaner, then rinsed thoroughly with deionized water, and subsequently dried at room temperature. The dry steel substrates may then be treated at 500° C. for 1 h.

The cleaned, or cleaned and heat-treated, steel substrates are flooded with the coating material. The coated steel substrates are dried at room temperature for 1 h, then heated from room temperature to 500° C. over 1 h, held at. 500° C. for 1 h, and then cooled to room temperature over 6 h.

The thicknesses of the thermally solidified coats are typically in the range 150–400 $\mu$m, depending on the support material used and the amount of coating material used.

F. Evaluation

Method of Determining the Deodorizing Activity

About 100 mg of the following test substances are introduced into a circulating-air oven preheated to 300° C. (catalyst temperature about 300° C., support: steel wire mesh):

pyrazine, thiazole, maltol, vanillin and 2,4-decadienal.

The test substances evaporate in the hot oven, with the vapours being passed as off-gases (off-gas flow: 0.5–1.2 l/s) by the stream of circulating air through an outlet port without a catalyst and an outlet port with catalyst to a downstream sample collector. The collected samples are analysed by means of GC-MS spectroscopy. The spectra are used to determine breakdown rates for the test substances in the off-gas stream that passes over the catalyst in comparison to the off-gas stream which does not pass over a catalyst (principle: relative measurement on an experimental system). The breakdown rates are indicated below in %.

| Catalyst | Pyrazine | Thiazole | Maltol | Vanillin | Decadienal |
|---|---|---|---|---|---|
| Pd/Pt cat (*1) | 0 | 0 | 90 | 90 | — |
| (*2) | 83 | 88 | 73 | 78 | 65 |
| (*3) | 69 | 56 | 74 | 70 | — |

(*1): Palladium, metallic, on steel wire nets, commercial catalyst
(*2): Inventive Mn/Co/Ce-MTKS sol cat., coating material of Example 1
(*3): Inventive Mn/Cu/Ce-MDKS sol cat., coating material of Example 3.

It is found that the catalytic compositions of the invention are capable of breaking down not only the other test substances but also heterocycles such as pyrazine and thiazole. This is not possible with commercially customary palladium catalysts. Also, with the catalytic compositions of the invention, there is no loss of catalytic activity after ten test cycles. In contrast, the commercially customary palladium catalyst is poisoned by heterocycles such as thiazole, losing catalytic activity with time.

Evaluation of the Oxidizing Capacity

[Test method according to DIN 51 171, "Testing of the self-cleaning capacity of continuously self-cleaning enamel coatings"]

Defined amounts (in each case 20–25 mg) of soya oil or engine oil are applied dropwise to the samples under investigation, at five points located on a circle, and after each dropwise addition are burnt by a one-hour heat treatment at 250° C., until a visible lustre appears as a result of the accumulation of unburned residues. The number of cycles until lustre occurs is used for the assessment.

| Coating | Oil | Number of cycles to lustre |
|---------|-----|----------------------------|
| (*1)    | Soya | 4–5 |
| (*2)    | Soya | 15–17 |
| (*3)    | Soya | 13–15 |

(*1): Commercially customary, oxidative enamel, containing Fe/Mn oxides
(*2): Catalytic composition 1
(*3): Catalytic composition 1, but using silica gel 40 as support material instead of alumina 90

The catalytic compositions of the invention (coat thicknesses between 150–400 micrometres) possess high absorbency, owing to the cavities which exist in the coating, and hence have a good spreading capacity for oils. In contrast, the glass-like enamels have a low absorbency and spreading capacity.

We claim:

1. A domestic appliance comprising a catalytic composition for deodorizing or oxidizing purposes, the catalytic composition comprising a coating of a coating material containing particles of at least one catalytically active transition metal oxdie on a support, prepared by a process comprising the steps of:
   (i) applying to the support a coating material comprising:
      (1) a polycondensate of
         (A) at least one silane of the formula $R_a$—Si—$X_{(4-a)}$ where each R, which may be the same or different, is a non-hydrolyzable group; each X, which may be the same or different, is a hydroxy group or hydrolyzable group; and a is an integer of 0 to 3 and is greater than 0 for at least 50 mol % of the silanes; or an oligomer derived therefrom, and
         (B) optionally, at least one compound of a glass-forming element, and
      (2) particles of at least one catalytically active transition metal oxide, the weight ratio of the particles of the at least one catalytically active transition metal oxide to the polycondensate being from 10:1 to 1:10; and
   (ii) thermally treating the applied coating material to form the coating, the catalytic composition being a component of the domestic appliance or of a device connected to the domestic appliance.

2. A domestic appliance of claim 1 where a is greater than 0 for between 50 mol % and 95 mol % of the silanes.

3. A domestic appliance of claim 1 where the at least one transition metal oxide is selected from the oxides of the metals La, Ce, Ti, Zr, V, Cr, Mo, W, Mn, Fe, Co, Ni, Cu, Ag and Zn, and mixtures thereof.

4. A domestic appliance of claim 1, where the particles of the at least one transition metal oxide have a diameter between 10 nm and 20 $\mu$m.

5. A domestic appliance of claim 1 where the coating has a thickness between 0.01 $\mu$m and 500 $\mu$m.

6. A domestic appliance of claim 1 where the support is composed of metal, metal oxide, glass, glass ceramic, ceramic or porous material.

7. A domestic appliance of claim 1 where the thermal treatment of step. (ii) occurs at between 200 ° C. and 700 ° C.

8. A domestic appliance of claim 1 where the coating material also comprises inorganic particles.

9. A domestic appliance of claim 1 where the coating is porous.

* * * * *